US010440958B1

(12) United States Patent
Yaniv et al.

(10) Patent No.: US 10,440,958 B1
(45) Date of Patent: Oct. 15, 2019

(54) DISINFECTANT MATERIAL COMPRISING A COPPER HALIDE SALT AND SURFACTANT

(71) Applicant: PEN Inc., Miami, FL (US)

(72) Inventors: Zvi Yaniv, Austin, TX (US); Dongsheng Mao, Austin, TX (US); Jason Avent, Austin, TX (US); Xueping Li, Austin, TX (US); Mocherla K. K. Rao, Hudson, OH (US); Stephanie Castro, Westlake, OH (US); Anand Upadhyaya, Broadview Heights, OH (US); Karl Rickert, Pompano Beach, FL (US)

(73) Assignee: Pen Inc., Deerfield Beach, FL (US)

( * ) Notice: Subject to any disclaimer, the term of this patent is extended or adjusted under 35 U.S.C. 154(b) by 0 days.

(21) Appl. No.: 15/351,979

(22) Filed: Nov. 15, 2016

Related U.S. Application Data

(63) Continuation-in-part of application No. 14/958,675, filed on Dec. 3, 2015, now Pat. No. 9,617,040.

(60) Provisional application No. 62/250,355, filed on Nov. 3, 2015, provisional application No. 62/155,872, filed on May 1, 2015, provisional application No. 62/087,990, filed on Dec. 5, 2014.

(51) Int. Cl.
*C11D 1/02* (2006.01)
*A01N 59/20* (2006.01)
*A01N 25/02* (2006.01)

(52) U.S. Cl.
CPC .............. *A01N 59/20* (2013.01); *A01N 25/02* (2013.01)

(58) Field of Classification Search
CPC .... C11D 1/02; C11D 3/43; C11D 3/48; C11D 9/36
See application file for complete search history.

(56) References Cited

U.S. PATENT DOCUMENTS

| 6,294,186 | B1* | 9/2001 | Beerse | A01N 43/36 424/401 |
| 9,615,572 | B1* | 4/2017 | Yaniv | A01N 25/06 |
| 9,617,040 | B1* | 4/2017 | Yaniv | B65D 25/38 |
| 2009/0263469 | A1 | 10/2009 | Rohrer | |
| 2016/0220728 | A1* | 8/2016 | Adams | A61K 8/25 |

FOREIGN PATENT DOCUMENTS

JP  2002119582 A  4/2002

OTHER PUBLICATIONS

Pramanik et al (Colloids and Surfaces B: Biointerfaces 96 (2012) 50-55).
Simionescu et al (Versatility of Silsesquioxane-Based Materials for Antimicrobial Coatings, Conference: 1st International Electronic Conference on Materials May 2014).
Li et al (Crystallization of ladderlike polyphenylsilsesuioxane (PPSQ)/isotactic polystyrene (i-PS) blends. Polymer 2001, 42(20), 8435-8441).

* cited by examiner

*Primary Examiner* — Charles I Boyer
(74) *Attorney, Agent, or Firm* — Loomis, Ewert, Parsley, Davis & Gotting P.C.; Mikhail Murshak

(57) ABSTRACT

A disinfectant material may be used to kill bacteria, viruses, mold and fungal contaminants while minimizing toxic risks to humans. The disinfectant material may be effective in killing pathogens and more on numerous types of surfaces including on the skin of mammals. Exemplary embodiments include a copper halogen, such as copper iodide. Exemplary materials may also include a pH stabilizer, a preservative, humectants, or other constituents. Exemplary disinfectant materials may be used as a liquid or a gel, applied via a wipe, sprayed or in other forms.

22 Claims, 4 Drawing Sheets

DISINFECTANT MATERIAL COMPRISING A COPPER HALIDE SALT AND SURFACTANT

TECHNICAL FIELD

This disclosure relates to a disinfectant material, which may be classified in U.S. Class 514 subclasses: 1, 724 and 772.3; and IPC A61K9/0014 and A61K9/06. Exemplary embodiments relate to a disinfectant material that may be used to kill bacteria, viruses, mold and fungal contaminants while minimizing toxic risks to humans.

BACKGROUND

Microbial life is abundant, tenacious, and often difficult to control. Organisms including bacteria and mold are often characterized by an ability to easily spread, rapidly reproduce, and thrive under conditions that can destroy higher life forms. Since some of these organisms cause human diseases, the exclusion or destruction of these organisms is important to prevent or block the spread of disease.

In addition to the problem of normal infections, the world is faced with a rapidly growing problem of "superbugs" or bacteria that have developed a resistance to one or more antibiotics or disinfectants. Many of these resistant microbes are acquired and spread in hospitals, oddices or other places were numerous people are often present. Commonly used sterilizing agents can include formaldehyde and glutaraldehyde, which are cancer causing, thus potentially placing people at risk. These agents may be highly reactive toward organic materials in general, and even some inorganic materials causing corrosion and erosion, and may also be toxic. Sometimes for surface treatment, such materials are applied to surfaces in different ways, which can sometimes cause the disinfectant material to be in contact with materials and animals which may potentially be undesirable.

Disinfectants and their use may benefit from improvements.

SUMMARY

Exemplary embodiments relate to disinfectant materials with antiviral, antibacterial, and antifungal properties. The exemplary material is effective for killing pathogens, and more, on numerous types of surfaces, including pathogens that may be present on human skin or the skin of other mammals. Exemplary materials may be housed in a container that includes a manually actuable dispenser such as a pump or a spout, may be embedded in porous materials such as cloth or wipes, may be sprayed onto surfaces, may be applied to the skin of mammals or may have numerous other forms.

In exemplary embodiments the materials may comprise a copper halogen, such as marshite (copper iodide). Exemplary materials include marshite mixed with a surfactant which facilitates cohesion to surfaces that are contacted with the material. Exemplary materials also includes a pH stabilizer, a preservative and a humectants, among other constituents.

Exemplary embodiments of materials described herein have numerous beneficial properties and uses.

DETAILED DESCRIPTION

An exemplary embodiment includes a disinfectant solution. The solution may be in wetted relation with a cloth. The cloth and solution comprise a wipe that can be moved in contact with a surface to cause a layer of the solution to be applied on the surface. The exemplary solution is operative to kill bacterial and fungal organisms.

Exemplary wipes may be held in and dispensed from liquid tight wipe containers. Two exemplary wipe containers are shown and described in FIGS. 1 and 2.

Figure 1:
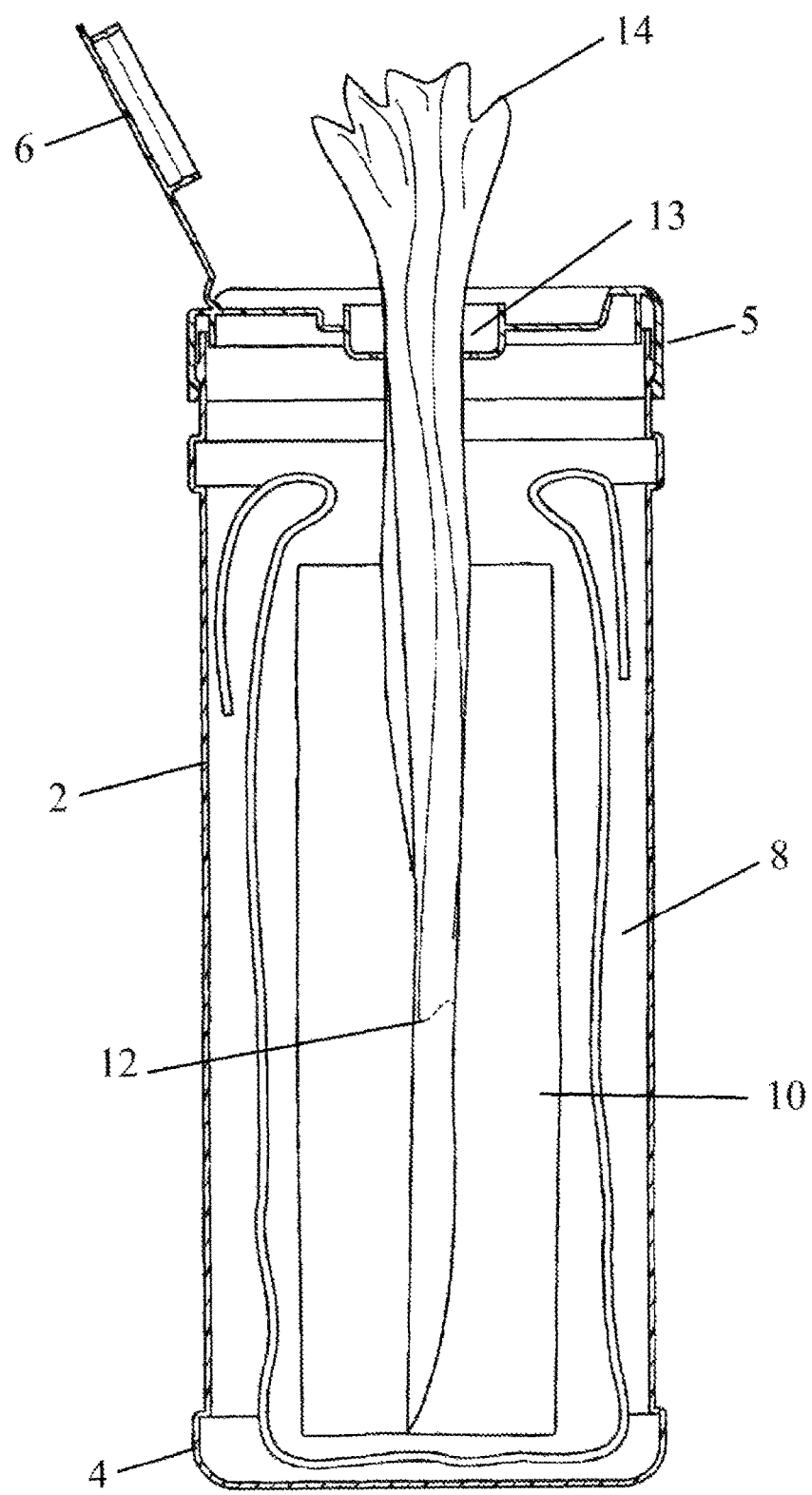
FIG. 1 is a cross-section view of an exemplary wipe dispensing container wherein the wipes are obtained from the top of a wipe container.

Referring now to the drawings, FIG. 1 shows an exemplary article of manufacture including a wipe holding container, as shown in cross section.

The exemplary wipe holding container includes a liquid tight cylindrical canister 2. The canister is closed at one end by a closed base 4. The canister is closed at an opposed end from the base by top 5. The top includes a resealable cap or lid 6.

The exemplary canister may be constructed of a plastic material, such as thermoformed material or blow-molded material, a carton material such as a lined paperboard, or a metalized or laminate structure, such as metalized or laminate film.

The exemplary wipe holding container includes an interior area 8. Area 8 houses a roll 10 of wipes. The wipe material of the roll is perforated with the perforations 12 set in a direction transverse to the length of the material web so that individual wipes 14 can be readily separated from the roll. The sheet-like fabric material of the exemplary embodiment is generally a nonwoven non-absorbent cloth material. The roll 10 of wipes is made such that it holds or is otherwise in wetted contact with the exemplary solution.

As shown in FIG. 1, the container holds the roll of moist wipes 10 in generally air tight relation when the cap 6 is closed. The top 5 is provided with an outlet opening 13 through which the moist wipes 14 are withdrawn. The outlet opening 13 can be selectively covered by the cap so the wipes remain wetted with the solution and do not dry out during storage.

Figure 2:
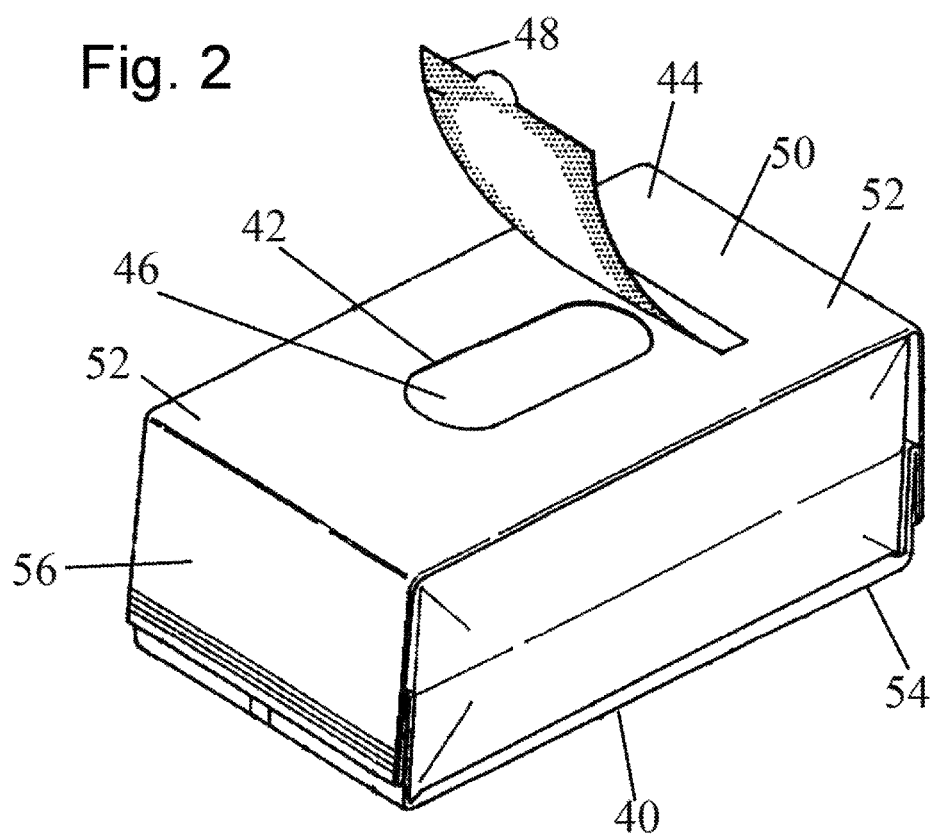
FIG. 2 is a view of an exemplary wipe holding container wherein the wipes are stacked in a wipe container.

Referring now to FIG. 2, an alternative exemplary wipe holding container 40 is shown. Container 40 includes a storing body 44 in which the wipes 42 are stored. The storing body 44 is provided with an outlet opening 46 through which the wipes 42 may be withdrawn. The outlet opening 46 is covered with an opening- and closing-cover label 48 detachably (or peelably) attached to the storing body 44.

In the alternative exemplary wipe dispensing container 40 according to this embodiment, the storing body 44 has a generally rectangular body formed from a generally square sleeve-like packing material with opposed ends. The outlet opening 46 is formed in a surface 50 of the packing material. Opposing side edge portions 52 of surface 50, and opposing side edge portions 54, are rigidly reinforced so that they exhibit self-supporting properties. The surfaces 50 and 54 are sealed at the opposed ends. Both sealed opposite ends 56, are fixed so that the one surface 50 forms two opposing end faces 56 (only one is shown) of the generally rectangular body.

The exemplary wipes 42 are comprised of non-woven fabric which is in wetted contact with an exemplary solution. The wipes 42 are stacked in an interleaved array and stored in the storing body 44 so that they can be withdrawn in a pop-up manner.

Other exemplary embodiments may include an article of manufacture which includes a wipe article held individually in a liquid tight container such as a flexible envelope. Such an envelope may hold the cloth wetted with the solution in an interior area thereof. The envelope may be initially sealed with the wipe therein to avoid the evaporation of constituents of the solution and to prevent contamination.

The envelope type container may be opened and the wipe removed from the interior area. The wipe may then be used to contact and transfer to a surface to be disinfected, the solution carried on the cloth. In exemplary arrangements the solution acts to kill bacterial, fungal and virus organisms on the surface. The exemplary deposited solution dries to leave a film on the surface which operates to provide continuing disinfecting properties in the manner hereinafter described.

Figure 3:
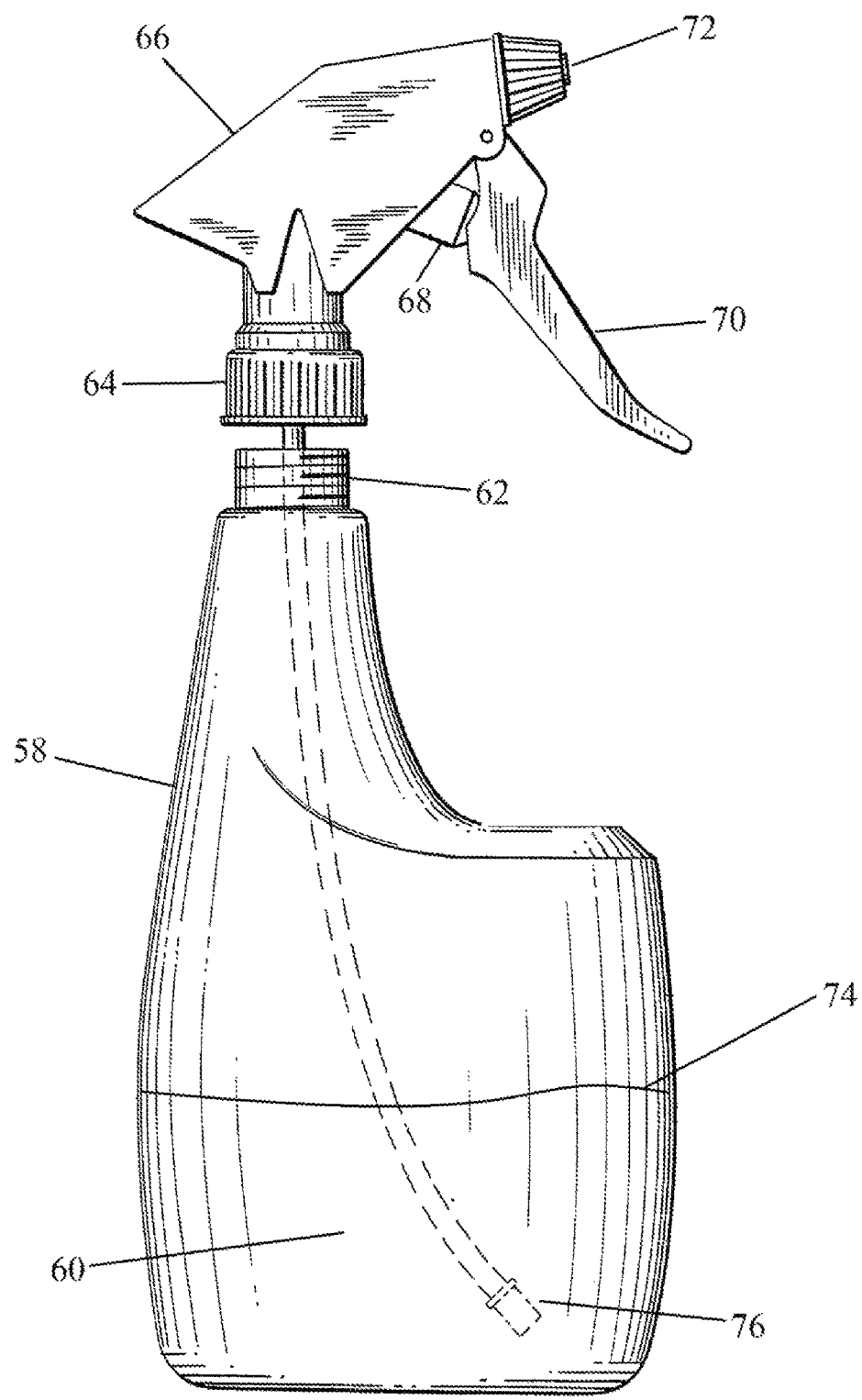
FIG. 3 is a view of an exemplary manually actuable atomizing sprayer in which a solution can be dispersed from the interior area.

Referring now to FIG. 3, an exemplary liquid tight container 58 is shown. The container bounds an interior area 60. At the top of the liquid tight container 58 there is a threaded neck 62. There is also a threaded coupling 64 attached to a dispensing element 66. The dispensing element is operative to dispense a disinfectant solution via a pump member 68 having an operating handle 70 and an atomizer 72. The interior 60 of the container 58 contains liquid solution which has a liquid level 74. A fluid inlet 76 in the interior area 60 is connected to the dispensing element 66. The solution or material may be drawn through the fluid inlet 76 by squeezing the operating handle 70, causing the pump member to cause the solution or material to pass out of the atomizer 72 and directed onto a surface desired to be treated. It will be understood that the dispensing element 66 is purely exemplary, and in other embodiments other types of dispensing means may be used, depending upon contemplated use of the device including being selectively directable.

Figure 4:
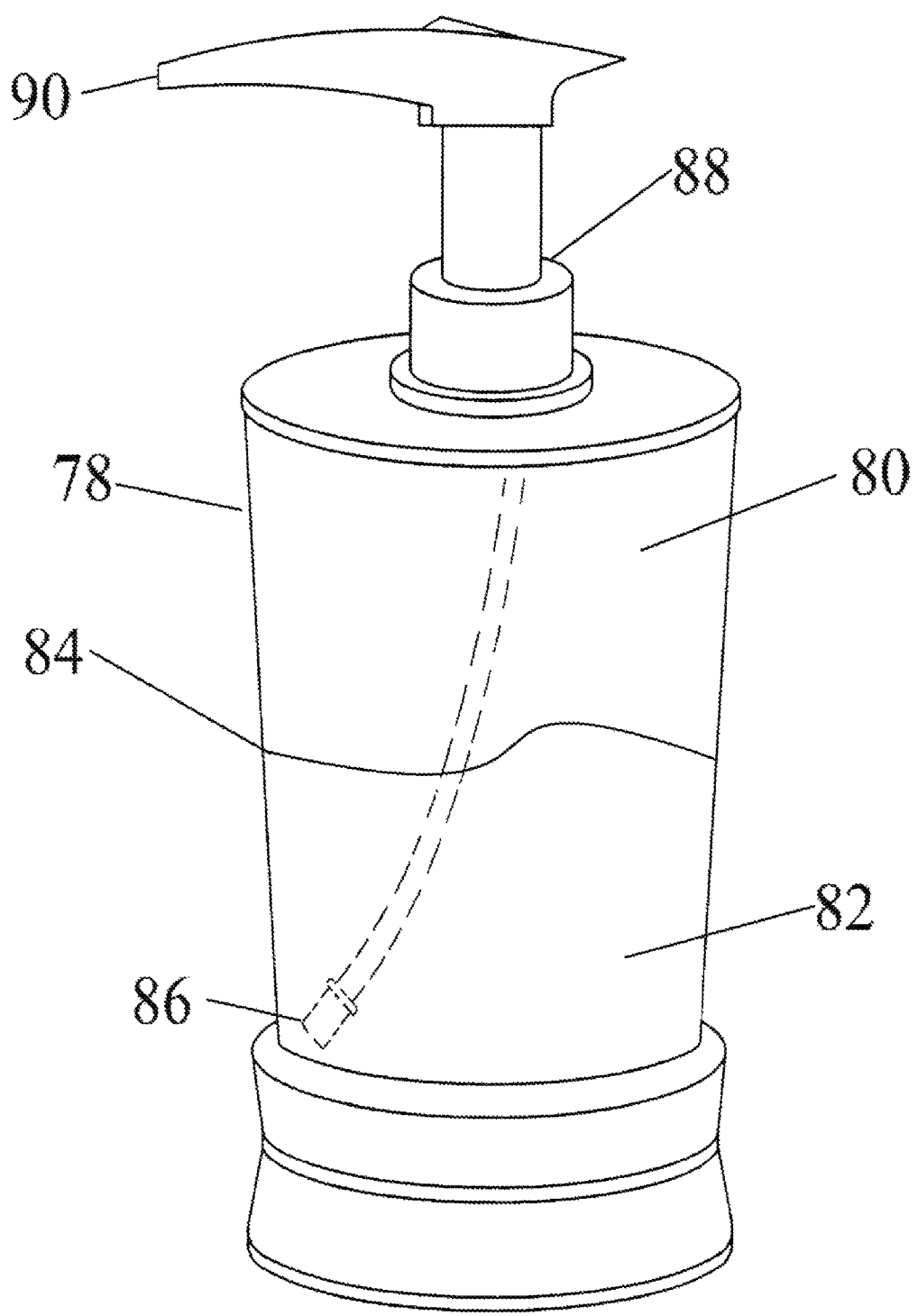
FIG. 4 is a view of a generally liquid tight container having a manually actuable pump mechanism designed to dispense a material from inside the container.

Referring now to FIG. 4, an alternative exemplary generally liquid tight container 78 is shown. The container bounds an interior area 80. Inside the interior area there is a liquid gel material 82 which comprises a disinfectant material which serves as a hand sanitizer and which has a level 84. Also inside the interior area there is a conduit having a fluid inlet 86. A manually actuable pump mechanism 88 extends on the outside of the liquid tight container. The manually actuable pump mechanism 88 is operative when actuated, to move material from the internal fluid inlet 86 to a fluid outlet 90 outside the interior area. It will be understood that the described embodiment is purely exemplary, and in other embodiments other dispensing means may be used, depending upon contemplated use of the device.

Of course the approaches described for producing and using these articles of manufacture in the form of disinfecting wipes, solutions, gels and their containers are exemplary, and in other embodiments other approaches may be used. For purposes hereof the terms solution and material providing disinfecting properties are used interchangeably.

The exemplary solution used includes a halogen copper salt, and in particular copper iodide. Copper is useful because it kills fungal infections, bacteria, molds and viruses including antibiotic resistant strains. The exemplary solution is operative to kill both enveloped and non-enveloped types of viruses as well as gram positive and gram negative bacteria. Copper kills all known types of harmful bacteria and it is believed that bacteria have been unable to develop any immunity to copper. Exemplary embodiments of some disinfectant materials do not include copper salts in a complex with benzoic acid or a benzoic acid analog.

The strong antiviral activities of copper and copper oxide are often enhanced at the nanoscale level (typically, particles having sizes less than 100 nanometers; such particles are also often referred to as "nanosized").

Exemplary embodiments of the solution include halogen copper salts, which are stable in air and in water. Such halogen copper salts may have enhanced antibacterial/antiviralantifungi/antimold activity not only because of a presence of copper ions, but also a presence of halogen ions. Herein, the terms "copper halide", "halogen copper salt" and "halogen copper" refer to a compound of copper with one of the halogen elements ("halogens"): fluorine (F), chlorine (Cl), bromine (Br), iodine (I), and astatine (At), plus the artificially created element 117 (ununseptium).

Copper ions, in particular the monovalent specie $Cu^+$, or cuprous, are able to kill bacteria, viruses, fungi and molds due to their oxidation from $Cu^+$ to the divalent specie $Cu^{++}$ (also referred to as $Cu^{2+}$ or cupric) and the associated generation of hydrogen peroxide in the presence of atmospheric oxygen and humidity. When this reaction occurs, the $Cu^+$ ion reacts with hydrogen peroxide, which oxidizes $Cu^+$ to $Cu^{++}$ producing a strong hydroxyl radical (i.e., resulting in strong (effective) oxidation power), which radical although unstable, is responsible for the bioactivity. The bioactivity referred to herein refers to the radical oxidizing biological matter (e.g., live organisms) to kill such organisms.

Generally, monovalent copper ($Cu^+$) in an aqueous solution tends to be converted to metallic copper, or $Cu^{++}$, by a disproportionate reaction. $Cu^+$ in aqueous solution may behave as a catalyst in a Fenton-like reaction. As a result of the oxidation of $Cu^+$ to $Cu^{++}$, the solution generates hydrogen peroxide ($H_2O_2$):

$$2Cu^+ + 2O_2 \rightarrow 2Cu^{++} + 2O_2^-$$

$$2O_2^- \rightarrow H_2O_2 + O_2$$

The hydrogen peroxide so formed then goes through a Fenton-like reaction leading to the generation of a hydroxyl radical OH. Hydroxyl radicals are highly reactive and, consequently, short lived. However, they form an important part of radical chemistry. The reaction is:

$$Cu^+ + H_2O_2 \rightarrow Cu^{++} + OH^- + \cdot OH$$

In the case that $Cu^{++}$ ions are returned to $Cu^+$ showing that $H_2O_2$ is catalytically decomposing to achieve hydroxyl radicals.

These reactions occur with marshite, or Cu, but are not unique thereto. Other $Cu^+$ halogen salts (e.g., CuCl, CuBr, etc.) may also be effective since each will deliver $Cu^+$. The halogen ion may also help the activity of $Cu^+$. In the specific case of CuI, for example, the iodide ion (I) is involved as explained below (the equations where X represents a halogen). In other exemplary embodiments of a copper based antibacterial/antiviral/antifungi/antimold agent, the copper halogen salts also produce a halogen ion ($X^-$). As a result, the following reaction occurs:

$$4X^- + 2Cu^{++} \rightarrow X_2 + 2CuX$$

In addition to having the molecular halogen in solution (for example, $I_2$), $Cu^{++}$ is returned to $Cu^+$, which will again participate in all the reactions previously disclosed.

Bacteria use an enzyme as a form of a "chemical lung" in order to metabolize oxygen. Due to the foregoing copper ion reactions, the strong hydroxyl radical destroys the "chemical lung" of the bacteria by stopping the take-up of oxygen. This effectively suffocates the bacteria in a matter of minutes, leaving surrounding tissue or material unaffected.

Fungi also survive by means of such a "chemical lung" much like bacteria. As a result, exemplary embodiments are also effective against fungi. Furthermore, exemplary embodiments are also effective against other molds.

A live virus will often take over another living cell and reprogram the nucleus of the cell to replicate the virus rather than the healthy cell. In this process, the cell reverses to a more primitive form that relies upon an oxygen metabolizing enzyme as a "chemical lung." This is similar to the bacteria case. Again, the copper ions stop oxygen from being brought into a virus producing cell, and the cell dies by "suffocation" (oxygen deprivation).

In some exemplary arrangements the solution includes a non-ionic surfactant. The interaction between a non-ionic surfactant and marshite particles is such that a non-polar alkyl tail of the surfactant is attracted to the hydrophobic surface of the copper iodide particles. When such solution is applied to a surface, some of these tails can have an orientation perpendicular to the marshite particle and some can be lying down on the surface. However, the anionic head of the surfactant will be attracted toward water, interacting with an aqueous environment through hydrogen bonding with the oxygen group.

In some exemplary arrangements the solution includes anionic surfactants. The molecular structure of anionic, or negatively charged, surfactants is one in which a negatively charged head group is bound to an inert, hydrophobic tail. When the solution is applied to a surface and the surface to be disinfected is positively charged, the surfactants in a CuI/water and isopropyl alcohol solution can form a nanofilm layer or bilayer in the presence of a polar solvent like water. This nanofilm layer or bilayer is a layer of copper ions surrounding water and surfactants. This layer or bilayer will form when the surfactant's concentration is close to or greater than the critical micelle concentration of the surfactant, which is approximately 0.3 g/L in the case of a water and isopropyl alcohol solution.

When a solution including a suspension of CuI in a water and isopropyl alcohol solution is applied to a surface and then excess is wiped off or the solvent mixture evaporates, the nanofilm layer or bilayer collapses causing the surfactants to be scattered on the surface. The negative head group attaches to the surface and the inert surfactant tail is randomly directed with respect to the surface.

On neutral surfaces like laminate, plastic, etc., due to the fact that there is no overall attraction between the surfactants and the surface, the surfactant is scattered on the surface, positioning sometimes with the tail on the surface, sometimes with the polar head toward the surface.

Finally, if the surface is negatively charged, the head group will be repulsed electro-statically from the surface and the tail will anchor the surfactants to the surface.

In an exemplary embodiment where a solution is made containing 0.1-0.5% surfactant in the solution by volume, the surfactant may contain both anionic and nonionic surfactants. The selection of a surfactant or combination of surfactants may be determined based on the desired formulation properties such as foaming ability, foaming retention, foaming stabilization, formulation stability, cleaning capabilities, and micelle stabilization.

Anionic surfactants are those with a negatively charged head and neutral (typically alkyl chain) tail. The negative charge of the head group is balanced by the presence of a cationic moiety. Examples of anionic surfactant groups usable in exemplary solutions include but are not limited to: phosphate esters, dioctyl sulfosuccinate, alpha olefin sulfonate, octane sulfonate, ethylhexyl sulfate, lauryl sulfate, laureth sulfate, and gluconate. Examples of cationic moieties that can be combined with anionic groups in exemplary solutions include but are not limited to: sodium, potassium, magnesium, ammonium and alkyl ammonium. Many types of anionic surfactants are commercially available and are best known for reduction of water surface tension and high foaming capacity.

Nonionic surfactants are those which carry no charge, however they still have a polar head and nonpolar tail. Examples of nonionic surfactants usable in exemplary solvents include but are not limited to: alkyl polysaccharides, sorbitan esters, polyethyleneoxy (PEO) sorbitan esters, PEO fatty acid esters, PEO fatty acids, PEO fatty alcohols, PEO synthetic alcohols, block copolymers of PEO and polypropyleneoxy (PPO) groups (PEO/PPO), alcohol ethoxylates, nonylphenolethoxylates, alkyl glucosides, and amide ethoxylates. Many types of nonionic surfactants are commercially available and typically function as foaming agents with foam stabilization properties.

An exemplary embodiment of the solution includes a pH stabilizer. A pH stabilizer will allow the pH of the solution to be maintained over a shelf life. Additionally, the pH stabilizer may adjust the solubility of other ingredients. The pH stabilizer will vary based on the solvents and surfactants used in the solution. The pH stabilizer will also vary based on the amount of copper iodide desired to be in solution. However, a wide variety of pH stabilizers may be used. In an exemplary embodiment, the pH stabilizer may have a concentration in a range of about 0.1-0.3% of the solution by volume. Examples of pH stabilizers that may be used in exemplary solutions include but are not limited to: citric acid, acetic acid, phosphoric acid, benzoic acid, ascorbic acid, sodium hydroxide, triethanolamine, glycolic acid, and ammonium hydroxide or mixtures thereof.

An exemplary embodiment of the solution includes a preservative. The preservative will allow the efficacy of the solution to be maintained over a shelf life. However, a wide variety of preservatives may be used. In exemplary embodiments, the preservative may have a concentration in a range of about 0.5-5% of the solution by volume. Examples of preservatives usable in exemplary solutions include but are not limited to: sodium hydroxymethylglycinate, polyaminopropylbiguanide, quaternary ammonium compounds, EDTA salts, EDTA fatty acid conjugates, alkanols especially ethanol, isopropyl alcohol, benzyl alcohol, parabens, sorbates, urea derivatives, and isothiazolinone, or mixtures thereof.

An exemplary embodiment of the solution includes a rheology agent, or additive. Rheology additives are used primarily to optimize the flow behavior in a particular application. This improves the processability and storage stability without settling, and enables a thicker application of layers. In exemplary embodiments the rheology additive may have a concentration of about 0.5-5% by volume in the solution as necessary to provide the desired properties. Examples of rheology agents include BYK-410 and BYK-D420 (both supplied by BYK Chemicals Wallingford, Conn., USA).

An exemplary embodiment of the solution includes a chelating agent. Chelating agents are ingredients that bind with metal ions or metallic compounds, preventing contamination or discoloration of the solution. Examples may include disodium EDTA, tetrasodium EDTA, tetrasodium glutamate diacetate, sodium citrate, sodium gluconate and sodium phytate or mixtures thereof.

An exemplary embodiment of a solution or a material used as a hand sanitizer or for another use in which skin contact will generally occur, includes humectants. Humectants (or moisturizers) allow a way to prevent loss of moisture thereby retaining the skin's natural moisture. Some compounds also have the ability to actively attract moisture. Examples may include propylene glycol, hexylene glycol, and butylene glycol, glyceryl triacetate, neoagarobiose, sugar alcohols (sugar polyols) such as glycerol, sorbitol, xylitol, maltitol, polymeric polyols such as polydextrose, quillai, urea, Aloe vera gel, MP diol, Alpha hydroxy acids such as lactic acid, and lithium chloride or mixtures thereof.

The exemplary solutions are intended to be environmentally friendly and safer than currently used disinfectant solutions. In exemplary solutions, the size of the marshite particles for suitable antiviral activity, safety and cost may be in a range between 300 nanometer and 4,000 nanometer in diameter. Furthermore, with some exemplary embodiments the total amount of copper ions potentially entering the environment from the application of the solution is restricted by using a copper salt with limited solubility in water or the other carrier solution—thus limiting the probability of excess copper ions leaching out or solubilizing directly into the environment.

Exemplary embodiments comprise a solution including marshite particles between 50 nanometer and 5,000 nanometers. When the size is decreased, only a small change in the percentage of surface molecules exists. However, due to nanoparticle safety concerns, the Federal Government and many other institutions have indicated concerns about particles having the diameter smaller than 300 nanometers. Therefore, in some exemplary embodiments of the solution CuI particles are selected to be in the size range larger than 300 nanometers to reduce these concerns.

By calculations and experimental results it has been determined that with 20 mg/L of marshite in an exemplary liquid test solution, the average distance between two particles of marshite is approximately 3 microns in the liquid solution and after applied to a surface in the dry film it is approximately 1 micrometer. The low concentration of 20 mg/L of active marshite in this exemplary embodiment is useful for keeping the environment green and safe. The size of H1N1 influenza virus is approximately between 100 and 125 nanometers. Thus in such exemplary solutions, once applied the probability of the virus coming into contact with the lethal marshite particles is high. However, this is merely one embodiment and other exemplary embodiments provide for a copper salt of limited solubility in an exemplary solution. This limited solubility resolves the risk of copper leaching into the environment.

In an exemplary embodiment of the solution, the copper iodide may make up about 0.005-5% of the total solution. However, this is limited by the solubility of the copper salt in the solution. It is possible to extend this range to up to 30% of the solution, however the concentration of the copper iodide actually in the solution as a result of the solubility will generally be in the range indicated.

In an exemplary wipe embodiment with a cloth that comprises a non-woven cloth, the solution is in wetted contact with the non-woven cloth, and the non-woven cloth is generally non-absorbent with respect to the solution. Generally non-absorbent nature of the non-woven cloth refers to the solution as a whole being less than 10% being absorbed into the cloth. Of course in other embodiments, other cloth types may be used. The cloth is such that in wiping the cloth against a surface, the solution will be deposited on the surface.

In some exemplary embodiments a fragrance is included in the solution. The fragrance may include any conventional fragrance that does not adversely affect a human. The fragrance in exemplary embodiments may have a concentration of about 0.1-2% by volume of the solution as necessary to provide the desired odor properties. Fragrances may be made from essential oils and isolates derived from botanical ingredients such as: flowers, fruits, sap, seeds or skin of the plant, as well as the bark, leaves, roots, resins or wood of certain trees. Fragrances may also be parabens, phthalates or synthetic musks.

In some exemplary embodiments, polyphenylsilsesquioxane, or PPSQ, is included in the solution. Polyphenylsilsesquioxane helps secure the attachment of the copper iodide to surfaces. Polyphenylsilsesquioxane also may limit the amount of copper ions exposed to the environment. In an exemplary embodiment PPSQ may have a concentration of about 0.1-50% by volume. In some exemplary embodiments, 3-methoxy-3-methyl-1-butanol, or MMB is included in the solution. In exemplary embodiments with MMB, after drying, a powerful, antimicrobial coating may be formed on a surface. This antimicrobial coating can be sprayed or coated in many ways on many different surfaces. In exemplary embodiments the solution may dry very quickly due to the presence of MMB. In another exemplary embodiment, the antimicrobial coating will strongly adhere to a coated surface after MMB evaporation due to the presence of PPSQ. In an exemplary embodiment it is possible to deliver a very powerful transparent coating on any type of surface, including painted surfaces, with no cosmetic alterations. In an exemplary embodiment, the concentration of MMB may be any amount up to 99.9%

In some exemplary embodiments, carbomers are added to a material. Carbomers are polymers of acrylic acid cross-linked with an unsaturated polyfunctional agent such as a polyallyl ether of sucrose. These carboxy vinyl polymers have the CTFA (Cosmetic, Toiletry and Fragrance Association) adopted name of carbomer molecules, converting the acidic carbomer salt. Carbomer thickening agents are commercially available under the trade names Carbopol® 934, 940, 941, 951, ETD 2020, ETD 2010, ETD 2001, and Ultrez™ from Lubrizol of Wickliffe, Ohio. Other thickening polymers and gums may be used according to their compatibility with the hydroalcoholic system. Examples of other suitable gelling agents include cellulosic ether polymers sold by Dow Chemical as Methocel® and hydroxymethyl, hydroxyethyl and hydroxypropyl cellulose gums sold under the mark Aqualon®.

In an exemplary embodiment, a base is used to convert the carbomer. Sodium hydroxide and Potassium hydroxide are only recommended for hydroalcoholic systems comprising up to about 20% and about 30%, respectively, alcohol. Likewise, sodium hydroxide, triethanolamine, monoethanolamine, and dimethyl stearylamine are not compatible as neutralizing agents because they do not adequately form a gel of desirable viscosity in a 60% ethanol composition. Other potential bases are tria amino, amino methu propanol, neutrol TE, diisopropanolamine, triisopropanolamine, Ethomeen C-25 or mixtures thereof.

In an exemplary embodiment, ethanol or other alcohols may be added to the material. This may be done in order to reduce the viscosity of the material to a more desirable level.

Some exemplary embodiments may provide a spray of a solution to be distributed on a surface to be disinfected. The surface may then be left to air dry, or wiped up with an absorbent towel or cloth. This leaves a solution film on the surface.

Some exemplary embodiments enable a wipe to contact a surface. The wipe is removed from a fluid tight container, and rubbed against a surface to be disinfected. The wipe leaves a film of the solution on the surface.

In further alternative embodiments a solution is incorporated into a paint or other surface coating. This paint may then be applied to walls or surfaces desired to be rid of microbes for an extended period of time.

Further alternative embodiments enable dispensing a material that can be applied directly to skin of humans or other mammals. For example, the material can be a hand sanitizer or other sanitizer that may be dispensed from a liquid tight container and placed on the hands of a human and/or applied to areas of the human or animal body.

Fibrous materials utilized in products such as textiles, carpets, filter materials, etc. may also benefit from being rid of viruses, bacteria, undesirable organic molecules or volatile organic compounds. Materials including marshite may be used in combination with other ingredients in order to achieve this result. Marshite is not a highly hygroscopic molecule; therefore, its efficacy as a catalyst is limited by the duration of moisture retention while it is in contact with the undesirable organic molecules (UOMs) that are to be oxidized. This means that the desired properties of marshite are not consistent given variations in humidity as well as the reservoir of moisture that may be available in the substrate to which the material is applied. Without the presence of moisture, oxygen, and a catalyst for an adequate duration of time, the marshite may be ineffective. Furthermore, in alternative embodiments it is desirable that copper iodide particles be attached to the fibers for an extended period, not only due to the catalytic activity of marshite, but also because the particles are physically attached to the fibers. By allowing moisture and oxygen to be present, the copper iodide will react with the UOMs.

Similarly, in some situations it can be difficult keeping the UOMs in contact with the marshite catalyst of oxidation long enough to ensure UOM destruction. Especially when volatile organic compounds (VOCs) are considered, in some situations there may not be enough time for the marshite to destroy the VOC, before the VOC adversely effects the environment or organisms within the environment.

Volatile organic compounds are problematic, especially as materials using solvents, plasticizers and other volatile chemicals are introduced into living or working environments. Compounding this issue, many buildings are virtually airtight; allowing VOCs to build up in the environment and in the people who spend time in them.

Systems have been designed to destroy VOCs using reactors. Some reactors utilize large beds of materials and energy input such as UV light or generated ozone to destroy VOCs. These can be problematic as residual ozone can be emitted into the areas occupied by people, leading to irritation of sinuses and many other problems associated with inhaled oxidizers. These systems often only treat some of the VOC burden in the air, as the concentrations of oxidizer are not high enough to achieve 100% destruction.

Some systems for VOC reduction are simply absorptive, such as carbon or zeolite. These systems decline in their efficiency to capture VOC over time, eventually leading to an ineffective system with a poor performance, unless VOC concentrations are monitored and the absorption medium replaced or replenished. Because VOC contamination is often heterogeneous, monitoring the effectiveness of absorptive filtration is problematic. Monitors most often detect specific compounds, meaning that to get a true detection across a wide range of hazardous VOCs can require sophisticated systems of detection. A combination of absorptive and oxidizing systems offer a synergy of functions that can lead to a much more complete capture and destruction of VOCs than either system alone. In addition, the use of an absorptive system means that much less energetic means of VOC destruction can be employed because the VOCs can be attacked over longer periods of time.

The catalysts of oxidation currently employed in some VOC reduction systems are usually disposed on solid substrates. These substrates can be textured to provide a large surface area, but to give the appropriate amount of surface area and contact time between the VOC and the solid substrate requires large reactors and can cause problems with resistance to air flow.

A system that retains the VOCs on the surface where the oxidation is catalyzed can utilize less energetic mechanisms than active systems using UV or ozone. This means a cleaner system that does not emit oxidizers into the environment and more complete oxidation of contaminants, since incomplete oxidation of VOCs can often create more hazardous compounds than no oxidation at all. In some exemplary systems, molecular oxygen can be used as the oxidizing agent and immobile, low-toxicity copper ions can be used as a catalyst. If the VOC's are captured by affinity to the solid substrate, then the problem of restriction in air flow can be avoided by using a simple coating on a filter or with a layer of material on the inside surfaces of an air duct system.

Alternative embodiments include a system in which an air duct coating is operative to inhibit the growth of microbes. Because surfaces inside air ducts are treated in a way that captures VOCs, the system has a much more functional role than simply preventing the growth of microbes on the surface of ventilation systems or reducing the growth of microbes on a filter. A system can be properly proportioned such that even at the maximum level of dust caking, the removal of VOCs will be adequate to decontaminate air in an average home or other generally closed structure.

Alternative embodiments may be used in a commercial or industrial setting. An air duct system can be properly proportioned such that even at the maximum level of dust caking, the removal of VOCs will be adequate to decontaminate air within an area in a commercial building or industrial setting.

Alternative embodiments may be used in confined structures or areas used in modes of transportation such as planes, trains, automobiles, busses, subway systems, light rail, ferries, or taxis. A system of air purifying can be properly proportioned such that even at the maximum level of dust caking, the removal of VOCs will be adequate to decontaminate air in a confined area associated with a mode of transportation.

Alternative embodiments include an antiviral/antibacterial material which will also be effective against organic residues on the fibers, thereby achieving a multifunctional agent that destroys pollutants as well as biological materials.

When organic compounds are suspended in a flowing liquid, the compounds may pass over a bed of marshite particles without enough time to react. This may mean a stain or other pollutant ends up disposed on a surface where its effect or appearance is undesirable, in spite of the effectiveness of marshite in destroying or precipitating the waterborne or other liquid borne pollutant if it were to remain with the marshite particles.

Alternative embodiments allow for an increase in the duration of moisture and organic compound retention in contact with the marshite material so that such material can have an adequate set of conditions (mainly moisture) and enough duration of contact with the organic compound to substantially destroy it. An alternative embodiment provides for a solution with a balance of moisture retention, surface area, trapping and catalysis on surfaces, all while being lower cost than an equivalent functioning pure marshite particle bed.

Alternative embodiments include a water based solution containing water, a surfactant, and 300-500 micrometer copper iodide particles. The role of the surfactant in this case is to create a complex molecular interaction between the copper iodide particles and water molecules. In such an embodiment, the copper iodide particles are surrounded by water molecules, which enable their catalytic activity.

With respect to attaching the marshite particles to fibers, alternative exemplary embodiments include a percentage of polyphenylsilsesquioxane that secures the attachment of the copper iodide particles to such fibers.

In order to have a water reservoir to facilitate marshite reactivity, multiple compounds may be used. For example, zeolite has an excellent mix of desirable properties containing many pores with different sizes, water holding capacity, surface area for gas adsorption and structures that may house CuI particles in the desired size range for slow release. Other materials that may be useful are synthetic and natural polymers, activated carbon, clay and pearlite, vermiculite as well as other suitable materials. These materials may be mixed and adsorbed with CuI in the suitable proportions to create cost effective, highest efficacy products for the catalytic application they are designed to perform.

In alternative embodiments, copper iodide may be incorporated with a hygroscopic compound. The association of copper iodide and hygroscopic agents will hold moisture and allow the catalytic effect of copper iodide to occur at the interface of the moist surface and atmosphere. In alternative embodiments the hygroscopic compound may be silica gel, zeolite and clay. Additionally, these hygroscopic compounds may be admixed with CuI to enhance oxidative catalytic properties through longer hydration times and rapid uptake of moisture.

In alternative embodiments, in addition to the retention of moisture, chemically reactive or chemically retaining compounds may be employed in order to capture odors or staining chemistries, allowing longer contact time for more complete destruction. For example, activated carbon provides a chemically absorbing scaffold and many internal channels that lead to dead ends within the structure described as "the tortuous path". The high surface area and porosity of these substrates make them excellent absorbers of chemicals, but they are eventually saturated with chemicals and this saturation reduces their effectiveness over time. Zeolites offer many of the same properties as activated carbon, and can increase the residence time of the volatile gasses and staining molecules within them, allowing the copper iodide to work more effectively and at lower concentrations than if it was applied alone.

In alternative embodiments, copper iodide is applied to a substrate that both adsorbs water and undesirable volatile chemicals which allows a very low loading of copper iodide to have a long-lasting effect. Zeolites and activated carbon utilized alone may have a short lifetime of effectiveness after they are saturated, but copper iodide offers a mechanism for destroying these adsorbed compounds. Therefore, if copper iodide's catalytic oxidation is balanced with the rate of loading of undesirable compounds into the adsorbent material, then the lifetime of the product is increased dramatically over any single-constituent solution.

When a product like zeolite or activated carbon is saturated with a solution of dissolved copper iodide, then dried in repeated cycles, there is an accumulation of copper iodide crystals on the inner surfaces as well as small particles trapped within their large pores. This combination of readily dissolved crystals and slowly dissolving particles provides quick activation of the copper iodide upon wetting followed by a sustained release of copper iodide from the copper iodide particles.

Additionally, in alternative embodiments, zeolite bound to copper iodide particles will filter colored (or staining) particles from water better than either zeolite or copper iodide alone, due to the reduction reaction occurring that precipitates molecules from the solution. After a period of time where drying of the zeolite occurs in air, the oxidation of the stain leads to a renewed absorptivity of zeolite that would not occur in zeolite which does not contain copper iodide.

Alternative embodiments may be used for cleaning, including difficult cleaning applications such as cleaning red wine stains on a carpet. The red color of the wine comes from anthocyan pigments (also called anthocyanins) that are present in the skin of the grape. Generally it is very difficult to clean red wine stains on carpets or other textiles. An alternative embodiment of provides for cleaning red wine stains on a carpet using a water based solution, containing surfactants and 100 mg/L copper iodide. The antiviral/antibacterial activity of CuI is achieved through a series of reactions of the transformation from $Cu^+$ to $Cu^{++}$ and vice versa happening in an aqueous solution as described above. In these reactions there is the presence of $H_2O_2$. More importantly the cyanin family of chemicals including the three variants of the chemical structures, whereby a nitrogen atom replaces a carbon atom and as a result the carbon atom is not fully saturated chemically, creates a positive charge around nitrogen substitute. Due to this nitrogen charged substitute in cyanin chemical structures, the red color of the wine is transferred to a colorless material.

This type of reaction will occur when dyes have a similar formula as the cyanin or they include a replacement of carbon in a carbon hydrogen chain with nitrogen.

Alternative embodiments are also useful for treating a fungus infection called *Candidiasis* or *Candida Albicans* with a water based solution containing a surfactant and copper iodide solution. It should be mentioned that this utility is not limited to just *Candidiasis* or *Candida Albicans*, as such alternative embodiments are effective for antiviral/antifungal/antibacterial eradication and also for treatment of fungus type of diseases (such as skin diseases) in animals and even in humans.

EXAMPLES

Exemplary embodiments of a disinfectant material utilizing the principals described herein are further illustrated by the following examples, which are set forth to illustrate the presently disclosed subject matter and are not to be construed as limiting.

Example 1

Preparation of a Water Based Solution:
Combine 95% deionized water with 5% isopropyl alcohol, 5-500 mg/L of Copper Iodide particles from 300-4000 nm in size and enough surfactant to allow the surfactant's concentration is close to or greater than the critical micelle concentration of the surfactant, which in the case of the water and isopropyl alcohol mixture is around 0.3 g/L.

An exemplary wipe as described above may be wetted so as to contain this water based solution. The wipe may be made of a non-woven cloth that is generally non-absorbent with respect to the solution. The solution may further include a pH stabilizer, a preservative, a rheology additive, fragrance, a chelating agent, or polyphenylpropylsilsequioxane.

An exemplary embodiment of the wipe may have a solution with the following approximate concentrations of the total solution by volume:
solvent(s): 25-99%,
surfactant(s): 0.1-0.5%,
pH stabilizer: 0.1-0.3%,
preservative: 0.5-5%,
copper iodide 0.005-5%,
rheology additive: 0.5-5%,
fragrance: 0.1-2%,
chelating agent: 0.02-0.3%,
polyphenylpropylsilsequioxane: 1-50%.

Alternatively, an exemplary spray disinfectant may be comprised of this water based solution. The solution may further include a pH stabilizer, a preservative, a rheology additive, fragrance, a chelating agent, or polyphenylpropylsilsequioxane.

Alternatively, a liquid gel material used in contact with surfaces including the skin of humans or other living animals may be comprised of this water based solution. The material may further include a pH stabilizer, a preservative, a carbomer polymer, a base, a rheology additive, fragrance, a chelating agent, humectants, or polyphenylpropylsilsequioxane.

An exemplary embodiment of such gel material may have a solution with the following approximate concentrations of the total solution by volume:
solvent(s): 25-99%,
surfactant(s): 0.1-0.5%,
pH stabilizer: 0.1-0.3%,
preservative: 0.5-5%,
copper iodide 0.005-5%,
rheology additive: 0.5-5%,
fragrance: 0.1-2%,
chelating agent: 0.02-0.3%,
polyphenylpropylsilsequioxane: 1-50%,
humectants: 0.1-5%.

Example 2

Preparation of an Alcohol Based Solution:
Combine 50-99% MMB (3-methoxy-3-methyl-1-butanol), 1-50% PPSQ (polyphenylpropylsilsequioxane) and 5-500 mg/L of Copper Iodide particles from 300-4000 nm in size.

An exemplary wipe as described above may be wetted with so as to contain this alcohol based solution. The wipe may be made of a non-woven cloth that is generally non-absorbent with respect to the solution. The solution may further include a pH stabilizer, a preservative, a rheology additive, fragrance, a chelating agent.

Alternatively, an exemplary disinfectant spray may contain this alcohol based solution. The solution may further include a pH stabilizer, a preservative, a rheology additive, fragrance, a chelating agent.

An exemplary embodiment of the spray may have a solution with the following approximate concentrations of the total solution by volume:
solvent(s): 25-99%,
surfactant(s): 0.1-0.5%,
pH stabilizer: 0.1-0.3%,
preservative: 0.5-5%,
copper iodide 0.005-5%,
rheology additive: 0.5-5%,
fragrance: 0.1-2%,
chelating agent: 0.02-0.3%,
polyphenylpropylsilsequioxane: 1-50%.

Alternatively, a liquid gel material for contact with surfaces including skin of humans or other living animals may contain this alcohol based solution. The material may further include a pH stabilizer, a preservative, a carbomer polymer, a base, a rheology additive, fragrance, a chelating agent, humectants, or polyphenylpropylsilsequioxane.

Example 3

Preparation of a Water Based Gelatin:
Combine 0.5-74.5% deionized water, 25-99% isopropyl alcohol, 0.5-5% of a rheology additive, such as BYK-D420 (supplied by BYK Chemicals Wallingford, Conn., USA) and 5-500 mg/L of Copper Iodide particles from 300-4000 nm in size and enough surfactant to allow the surfactant's concentration is close to or greater than the critical micelle concentration of the surfactant, which in the case of the water and isopropyl alcohol mixture is around 0.3 g/L.

An exemplary wipe as described above may be wetted with so as to contain this water based gelatin. The wipe may be made of a non-woven cloth that is generally non-absorbent with respect to the solution or gelatin. The gelatin may further include a pH stabilizer, a preservative, a rheology additive, fragrance, a chelating agent, or polyphenylpropylsilsequioxane.

Alternatively, a liquid gel material for application on surfaces including skin, may contain this water based gelatin. The material may further include a pH stabilizer, a preservative, a carbomer polymer, a base, a rheology additive, fragrance, a chelating agent, humectants, or polyphenylpropylsilsequioxane.

Example 4

Preparation of an Alcohol Based Gelatin:
Combine 45-94.5% of an alcohol such as MMB (3-methoxy-3-methyl-1-butanol), 5-50% PPSQ (polyphenylpropylsilsequioxane) and 0.5-5% of a rheology additive, such as BYK-410 (supplied by BYK Chemicals Wallingford, Conn., USA), and 5-500 mg/L of Copper Iodide particles from 300-4000 nm in size.

An exemplary wipe as described above may be wetted so as to contain this alcohol based gelatin. The wipe may be made of a non-woven cloth that is generally non-absorbent with respect to the solution or gelatin. The gelatin may further include a pH stabilizer, a preservative, a rheology additive, fragrance, a chelating agent, or polyphenylpropylsilsequioxane.

Example 5

Method of Treating a Carpet Pad with Copper Iodide:
Another exemplary embodiment provides for application of copper iodide into the carpet pad that goes under carpets. These carpet pads are usually comprised of bound pieces of recycled foam. The process of binding the foam can involve an adhesive or can be done using heat, or both.

The process of putting the foam scraps together offers an opportunity to introduce copper iodide without requiring large quantities that would be wasteful if copper iodide were introduced in the manufacturing of raw foam. Because the mechanical properties of the raw foam scraps are not changed in the production process, the characteristics of the carpet pad also do not change as long as the adhesion between pieces is not affected by the introduction of copper iodide. Addition of a material such as copper iodide to an adhesive or dusted into heat-welding manufacturing process generally has little or no production impact compared to introducing a reactive component to more delicate processes associated with initial foam production.

Likewise, the process of binding foam together creates paths and channels for fluids to flow between fragments of foam, meaning a higher dosing of copper iodide to any fluids that may leak into the foam pad, as these fluids will be captured in the channels between pieces of foam.

As a water-activated odor eliminating compound, copper iodide infused carpet pads can aid a homeowner or other user by reacting with odor causing liquids such as urine, beverages and water spills. Upon moistening, the reducing action of copper iodide will precipitate redox-active compounds from the liquid, retaining them within the pad, essentially purifying the liquid to prevent contamination of the structural material beneath the pad.

At the same time, the copper iodide in an exemplary pad will dissolve into the liquid and travel with it, providing an oxidizing catalyst when the liquid and oxygen from the atmosphere react. This "seeding" of the liquid spill as it passes through the pad may mean that the user never becomes aware of the spill, which can dry harmlessly if it does not cause visible discoloration of the carpet.

Wicking of the liquid up from the wet carpet pad and into the carpet above can cause copper iodide to migrate into the carpet as it dries and pulls liquid out of the carpet pad below. This migration of copper iodide from the carpet pad upward may eliminate odors and destroy discoloring agents within the liquid that might otherwise require extensive cleaning. If the user does drench and clean the spill with water, this will enhance the migration of copper iodide into the carpet fibers as wicking and drying create deposits within the carpet fibers. In situations where the same area is urinated on repeatedly, this means the effect of the copper iodide migrating from the carpet pad will increase proportionally with each incident.

In another example, a spot of buck (deer) urine was placed on different carpet squares. Every spot was created by 10 ml of buck urine and for each liquid treatment the same sprayer was utilized to apply 10 sprays for each sample of treatment. Half an hour later, the spot treated with a mixture of water, surfactant, 3-methoxy-3-methyl-1-butanol, and polyphenylpropylsilsequioxane showed strong activity for removing the stain. After six hours, the stain was almost entirely eliminated. After twelve hours, the stain was completely eliminated. The odor of the sample was diminished after the first hour, and non-existent after six hours.

Example 6

Method of Retaining and Destroying Volatile Organic Compounds:

In another alternative exemplary embodiment, an antiviral and antibacterial material is effective to remove/eliminate/lessen/neutralize organic residues on fibers. The residues which may be effectively treated include undesirable organic molecules, pollutants, biological materials and volatile organic compounds. The fibers upon which the material may be effective include fibers upon which such residues accumulate such as carpet and ventilation filters.

Example 7

Experimental Test Against Feline Calcivirus ATCC VR-782

Copper ions (20 mg/L) in a water based solution were applied to a surface with the non-enveloped feline calcivirus ATCC VR-782. In 10 minutes an 82.22% reduction relative to the control after the exposure of the antimicrobial substance to the virus according to Modified ASTM E1053 that looks at the antiviral activity of an agent for 24 hours. In our case we wanted to have an idea about the rate of killing and this is why we limited the test to 10 minutes.

Example 8

Experimental Test Against H1N1 Influenza A, Strain A-California, and Human Corona Virus 229E.

A number of other tests were performed against H1N1 Influenza A, Strain A-California, and Human Corona Virus 229E. In the case of H1N1 Influenza A, towelettes embedded with water based solution of copper iodide at 20 mg/L showed according to modified test AATCC 100 a 99.7% reduction vs time zero control.

In the case of Human Corona Virus 229E according to modified ASTM E1053 the percent reduction was 99.99% in 10 minutes.

Of course it should be understood that Examples 1-8 are merely exemplary embodiments, and the inventive principles described may be applied to numerous other applications, uses, materials, situations, methods, compositions and articles of manufacture.

In some exemplary embodiments the concentration of marshite in solution is larger than 7 mg/L and smaller than 1 g/L.

In exemplary embodiments solution mixtures including copper iodide can be made into various forms including, but not limited to, foam, gel, cream, gelatin, spray, aerosol, bar, liquid, solid, gaseous, or other forms.

Exemplary solutions may be placed on or applied to any surface on which it is desired to be rid of virus, bacteria, mold or fungus. These surfaces may include, but are not limited to, glass, plastic, carpet, stainless steel, aluminum, walls, wood, clothing, floors, cloth, tile, porcelain, granite, quartz, cement, laminate, brick, stone, terrazzo, clay, ceramic, slate, limestone, marble, concrete, and metal.

Exemplary solutions may be placed on or embedded in surfaces at the time of manufacture of such surfaces in order to remove the virus, bacteria, mold or fungus.

Exemplary solutions may be applied in various ways, including, but not limited to, spray, brush, rolled, immersed, painted, propelled, coated, wiped, applied by hand, rubbed onto a surface, and placed on top of a surface.

Exemplary solutions may be deployed on or applied to filters, which may be in any form of air handling which may be found in homes, commercial facilities, industrial facilities, transportation facilities, vehicles, government buildings.

Exemplary solutions may be deployed in the healthcare industry on such surfaces such as those found in hospitals, clinics, emergency care facilities, doctor's offices, nursing homes, and veterinary services.

Exemplary solutions may be deployed in the transportation industry on such surfaces such as those found in taxis, busses, trams, boats, streetcars, subways, airplanes, airports, bus depots, dock, ferries, bus coaches, metro trains, train and subway platforms and trains including ticket and service counters and booths.

Exemplary solutions may be deployed in the education industry on such surfaces such as those found in public schools, private schools, higher education establishments, colleges, community colleges, day care, child care, and trade schools.

Exemplary solutions may be deployed in the food processing industry in such surfaces such as those found in a slaughter house, a meat packing plant, a cannery, a fish processing facility and a food packaging plant.

Exemplary solutions may be deployed in the livestock industry in such surfaces such as those found while engaging said livestock, or on the skin of livestock or other animals.

Exemplary solutions may be deployed on or applied to air vents, conduits, filters contained in air conditioning or furnaces.

Exemplary solutions may be deployed on stains caused by dyes, wine, or other undesirable colors in fibers or fabric.

Exemplary solutions may be applied to human skin or the skin of other living animals for treating acne, fungal infections and other skin diseases.

Exemplary solutions can include other, non-essential ingredients such as, but not limited to, fragrances, colorants, pH buffers, and the like for aesthetic or other purposes.

Exemplary solutions may have a reservoir material operative to sequester water and such materials may include, but are not limited to: zeolite, synthetic polymers, natural polymers, activated carbon, pearlite, vermiculite, silica gel and clay.

When used herein, neutralization is a term construed to mean to destroy, to neutralize, to reduce, to break apart, to eliminate, to negate, to nullify, to remove, to reduce, to make harmless and other meanings to those skilled in the art.

Of course these described embodiments are exemplary and alterations thereto are possible by those having skill in the relevant technology.

Thus the example embodiments and arrangements achieve improved capabilities, eliminate difficulties encountered in the use of prior articles and methods, and attain the desirable results described herein.

In the foregoing description, certain terms have been used for brevity, clarity and understanding. However, no unnecessary limitations are to be implied therefrom because such terms are used for descriptive purposes and are intended to be broadly construed.

Moreover the descriptions and illustrations herein are by way of examples and the inventions not limited to the features shown and described.

Further, it should be understood that components, materials, features and/or relationships associated with one embodiment can be combined with components, materials, features and/or relationships from other embodiments. That is, various components, materials, features and/or relationships from various embodiments can be combined in further embodiments. The inventive scope of the disclosure is not limited to only the embodiments shown or described herein.

Having described the features, discoveries and principles of the exemplary embodiments, the manner in which they are made, utilized and carried out, and the advantages and useful results attained, the new and useful articles, arrangements, combinations, methodologies, structures, devices, elements, combinations, operations, processes and relationships are set forth in the appended claims.

We claim:

1. An anti-microbial material disinfectant solution comprising:
   (a) an anti-microbial copper composition having:
       nanoparticles of copper halide salt that are able to produce copper ions,
           wherein the copper ions are in a form of cuprous ions,
           wherein the cuprous ions transform into cupric ions in the presence of a microbial,
               wherein the transformation of cuprous ions to cupric ions occurs by a Fenton-type reaction,
               wherein the cupric ions reverse back catalytically to cuprous ions in the presence of a halogen, and
               wherein the surface of the copper composition particles are hydrophobic;
   (b) a polar solvent that comprising water or alcohol forming a water or alcohol based solution,
       wherein the copper composition has a concentration of 5 to 500 mg per liter of the solution; and
   (c) an anionic surfactant with an alkyl non-polar tail,
       wherein the copper composition particles interact with the anionic surfactant and the non-polar tail of the surfactant is attracted to the hydrophobic surface of the copper composition particles, and
       wherein the anionic surfactant is provided in the solution at a concentration of 0.1% to 0.5%;
   (d) Polyphenylsilsequioxane at a concentration of 0.1 to 50% of the solution by volume;
       wherein the polar solvent, anionic surfactant, and copper composition particles come together to form a complex that traps the polar solvent in the immediate surrounding volume of the copper composition particles.

2. The anti-microbial material disinfectant solution of claim 1,
   wherein the copper composition is provided in a concentration of 20 mg per liter of the solution.

3. The anti-microbial material of disinfectant solution claim 1,
   wherein as a result of the transformation of cuprous ions to cupric ions by a Fenton-type reaction, hydroxyl radicals are created.

4. The anti-microbial material disinfectant solution of claim 1,
   wherein the copper composition has anti-fungal activity.

5. The anti-microbial material disinfectant solution of claim 1,
   wherein the copper composition has antibacterial activity,
       wherein the antibacterial activity occurs with respect to Gram Positive and Gram Negative bacteria.

6. The anti-microbial material disinfectant solution of claim 1,
   wherein the copper composition has antiviral activity,
       wherein the antiviral activity occurs with respect to enveloped and non-enveloped viruses.

7. The anti-microbial material disinfectant solution of claim 1,
   wherein the copper composition, combined with the one anionic surfactant in the presence of the polar solvent forms a nanofilm layer on positively and negatively charged surfaces.

8. The anti-microbial material disinfectant solution of claim 7, wherein the polar solvent is water.

9. The anti-microbial material disinfectant solution of claim 1, wherein the particle size of the copper halide salt is between 50-5000 nm.

10. The anti-microbial material disinfectant solution of claim 1, wherein the Polyphenylsilsesquioxane is between 0.1%-20% of the solution by volume.

11. The anti-microbial material disinfectant solution of claim 1 wherein the copper halide salt is not in a complex with benzoic acid or a benzoic acid analog.

12. The anti-microbial material disinfectant solution of claim 1 wherein the material does not include benzoic acid or a benzoic acid analog.

13. An anti-microbial material disinfectant solution comprising:
   (a) nanoparticles including copper and a halogen, the particles being operable to produce copper ions,
      wherein the copper ions are in a form of cuprous ions,
      wherein the cuprous ions transform into cupric ions in the presence of a microbial,
         wherein the transformation of cuprous ions to cupric ions occurs by a Fenton-type reaction,
            wherein the cupric ions reverse back catalytically to cuprous ions in the presence of the halogen; and
   (b) a polar solvent comprising alcohol or water forming a solution, wherein the copper composition has a concentration of 5 to 500 mg of the copper composition per liter of the solution; and
   (c) a surfactant operable to facilitate cohesion of the material to a surface, the surfactant provided in the solution at a concentration of 0.1% to 0.5% and operable to form a complex that traps the solution in the immediate surrounding volume of the particles;
   (d) polyphenylsilsequioxane at a concentration of 0.1 to 50% of the solution by volume:
      wherein the disinfectant solution is operable to form a nanofilm layer on positively and negatively charged surfaces.

14. The anti-microbial material of claim 13, wherein the copper and the halogen are provided as at least one copper halide salt.

15. The anti-microbial material of claim 14, wherein the particle size of the copper halide salt is between 50-5000 nm.

16. An anti-microbial material comprising,
an anti-microbial copper composition, including particles that are able to produce copper ions,
   wherein the copper ions are in a form of cuprous ions,
   wherein the cuprous ions may be transformed into cupric ions,
      wherein the transformation of cuprous ions to cupric ions occurs by a Fenton-type reaction,
      wherein the cupric ions may reverse back catalytically to cuprous ions
and an alcohol based solution,
   wherein the solution comprises 3-methoxy-3-methyl-1-butanol in an amount between 80% and 99.9% of the solution by weight,
wherein the copper composition has limited solubility in the solution,
   wherein the limited solubility is below 50 mg of the copper composition per liter of the solution.

17. An anti-microbial material disinfectant solution comprising:
   (a) copper iodide salt particles operable to produce copper ions,
      wherein the copper ions are in a form of cuprous ions,
         wherein the cuprous ions transform into cupric ions,
         wherein the transformation of cuprous ions to cupric ions occurs by a Fenton-type reaction,
         and wherein the cupric ions reverse back catalytically to cuprous ions;
   (b) a water or alcohol based solution, wherein the copper iodide salt has a concentration of 5 to 500 mg of the copper iodide salt per liter of the solution;
   (c) at least one surfactant operable to facilitate cohesion of the material to a surface, wherein the surfactant is provided in the solution at a concentration of 0.1% to 0.5%; and
   (d) at least one member selected from the group consisting of a pH stabilizer; a preservative, a rheology agent, chelating agent, a humectant, and combinations thereof;
   (e) polyphenylsilsequioxane at a concentration of 0.1 to 50% of the solution by volume;
   wherein the material is operable to form a nanofilm layer on positively and negatively charged surfaces.

18. A wetted cloth forming a wipe comprising the anti-microbial material disinfectant solution of claim 1.

19. A liquid solution in a liquid dispenser having an atomizer dispensing element comprising the anti-microbial material disinfectant solution of claim 1.

20. A liquid gel as a hand sanitizer comprising the anti-microbial material disinfectant solution of claim 1.

21. The anti-microbial material disinfectant solution of claim 1, wherein the anionic surfactant is selected from the group consisting of phosphate esters, dioctyl sulfosuccinate, alpha olefin sulfonate, octane sulfonate, ethylhexyl sulfate, lauryl sulfate, laureth sulfate, and combinations thereof.

22. A method of disinfecting a surface, the method comprising:
   (a) providing an anti-microbial disinfectant solution having a water or alcohol based comprising:
      (i) copper halide salt particles that produce copper ions in a form of cuprous ions, the copper halide salt particles having a concentration of 5 to 500 mg per liter of the solution;
      (ii) an anionic surfactant with an alkyl non-polar tail configured to facilitate cohesion of the material to a surface provided in the solution at a concentration of 0.1% to 0.5%; and
      (iii) a polar solvent, wherein the polar solvent, anionic surfactant, and copper iodide salt particles come together to form a complex that traps the polar solvent in the immediate surrounding volume of the copper iodide salt particles; and
      (iv) polyphenylsilsequioxane at a concentration of 0.1 to 50% of the solution by volume;
   (b) applying the antimicrobial disinfectant solution to the surface;
   (c) forming a nanolayer of the disinfectant solution on the surface;
   (d) exposing the surface to a microbial;
   (e) transforming the cuprous ions into cupric ions in the presence of the microbial, wherein the transformation of cuprous ions to cupric ions occurs by a Fenton-type reaction; and
   (f) catalytically reversing back the cupric ions to cuprous ions in the presence of the halide.

* * * * *